United States Patent [19]

Miyamoto

[11] Patent Number: 5,702,915
[45] Date of Patent: Dec. 30, 1997

[54] TOXICITY DETECTING BIOSENSOR SYSTEM

[75] Inventor: Shigeyuki Miyamoto, Tokyo, Japan

[73] Assignee: NEC Corporation, Tokyo, Japan

[21] Appl. No.: 542,021

[22] Filed: Oct. 12, 1995

Related U.S. Application Data

[63] Continuation of Ser. No. 187,473, Jan. 28, 1994, abandoned.

[30] Foreign Application Priority Data

Mar. 15, 1993 [JP] Japan ............... 5-053862

[51] Int. Cl.$^6$ ............... C12M 1/34; C12M 1/36; C12Q 1/18; C12Q 1/20
[52] U.S. Cl. ............... 435/32; 422/82.09; 435/33; 435/286.1; 435/288.1; 435/288.3; 435/288.7
[58] Field of Search ............... 422/82.09; 435/29, 435/32, 33, 286.1, 288.1, 288.2, 288.3, 288.4, 288.7

[56] References Cited

U.S. PATENT DOCUMENTS

| | | | |
|---|---|---|---|
| 3,370,175 | 2/1968 | Jordon et al. | 435/291 |
| 4,720,463 | 1/1988 | Farber et al. | 435/291 |
| 5,169,601 | 12/1992 | Ohta et al. | 435/291 |
| 5,278,048 | 1/1994 | Parce et al. | 435/29 |
| 5,589,352 | 12/1996 | Breznak et al. | 435/34 |

FOREIGN PATENT DOCUMENTS

| | | | |
|---|---|---|---|
| 567231 | 10/1993 | European Pat. Off. | 435/291 |
| 2047401 | 11/1980 | United Kingdom | 435/291 |

*Primary Examiner*—Jeffrey E. Russel
*Attorney, Agent, or Firm*—Young & Thompson

[57] ABSTRACT

A biosensor for detecting the toxicity of a sample includes a solid-state area image pickup element, a culture container positioned on an upper surface of a light-receiving portion of the element, at least a bottom surface of the culture container being formed of transparent material, a cell cultured in the culture container, and culture medium for growing the cell.

17 Claims, 3 Drawing Sheets

TOXICITY DETECTING BIOSENSOR SYSTEM

This application is a continuation of application Ser. No. 08/187,473, filed Jan. 28, 1994, now abandoned.

BACKGROUND OF THE INVENTION

1. Field of the Invention

The invention relates to a biosensor, and in particular, to a biosensor for comprehensively detecting cytotoxin, and also relates to a method for detecting cytotoxin by virtue of bio-related technology.

2. Description of the Related Art

Many and various chemical substances have recently been manufactured for use in medicine, and hence it is quite important to inspect the toxicity and carcinogenicity thereof to organisms. Presently, most of the tests for toxicity and carcinogenicity are accomplished by animal tests using rats and mice etc. A test to be accomplished outside organisms using animal cells is now studied as an alternative to or in addition to animal tests. For example, if hepatotoxin such as carbon tetra chloride ($CCl_4$), which causes hepatitis, is introduced into liver cells of a mature rat, there can be observed a leak-out and change of cell morphology of enzymes such as glutamic-pyruvic Transaminase (GPT), glutamicoxaloacetic Transaminase (GOT) and lactate dehydrogenase (LDH). Based on this fact, there has been proposed a possibility of detecting hepatotoxin. See the book "Experiments of a first generation culture liver cells" authored by Toshikazu Nakamura and issued by Gakkai Shuppan Center.

A biosensor has been developed for simply and rapidly detecting organic substances, in particular organism-related substances, and some of the biosensors are put to practical use. The one being developed most eagerly is an enzyme sensor utilizing the fact that enzyme has a high substrate specificity. A typical enzyme sensor has an enzyme-immobilized membrane on an electrode and acts according to the principle that the electrode detects the production of electroactive substances during enzyme reaction occurring in the enzyme membrane. A glucose sensor and an urea sensor are also being developed based on the above mentioned principle. In addition, a microorganism sensor is also being developed using microorganisms such as yeast, instead of enzyme. For example, respiratory activity of a microorganism may be measured by the oxygen consumption thereof by means of a combination of an immobilized microorganism membrane and an oxygen electrode. This is applied to a measurement of biochemical oxygen demand (BOD). See the book "Siosensor" authored by Shuichi Suzuki and issued by Kodansha as a series of "Kodansha Scientific".

It is a known technique to detect various conditions of cells including cell activity by inspecting data acquired about cell morphology. For example, Japanese Patent Public Disclosure No. 54-161991, which was laid open on Dec. 12, 1979, suggests this technique. In this Disclosure, while a sample is moved at a constant speed, information about a form thereof is read through a line scan type element for taking photographs of images of a solid. The cells are inspected using photographs taken with the element.

After charge coupled device (CCD) have been made available, the element for taking photographs of images of a solid has developed and has been enormously improved. The element is a little bit inferior to a conventional camera tube in terms of resolution, but superior to in terms of ease of handling, printing with intensive light and deflection of images. Because of these advantages, the element for taking photographs of images of a solid is taking over camera tubes in the field of broadcasting and so on.

The above mentioned conventional toxicity detecting test using animal tests has had many problems. For instance, it costs a lot to purchase animals and build equipments for feeding animals, and it takes a lot of time to determine whether a sample has toxicity or not due to a lack of quantitative results in the test.

A toxicity test using animal cells can resolve the above mentioned problems to some extent, however, it required the procurement of cells and samples, culture, and measurement of cells' activity, and hence is not a simple test.

An enzyme sensor can detect biological substances easily and rapidly. However, enzymes for use in an enzyme sensor are limited to stable enzymes which produce products which can be detected with an electrode, and accordingly an enzyme sensor can detect only limited substances. In addition, an enzyme sensor can theoretically detect only one substance, and accordingly cannot evaluate overall toxicity of an unknown sample. In other words, if a sample is expected to include therein various substances having various cytotoxins added at different rates, all toxic substances have to be identified first and then an amount of each substance needs to be measured by means of an enzyme sensor for use of the particular substance. Finally, it can be determined whether the sample has toxicity or not based on the results. Thus, the test using an enzyme sensor needs a quite complicated process.

A microorganism sensor can detect the toxicity of an unknown sample to microorganism. However, the toxicity to animal cells is not always consistent quantitatively and qualitatively with the toxicity to microorganism, and hence it is difficult to accurately detect the cytotoxin.

SUMMARY OF THE INVENTION

It is an object of the present invention to provide a biosensor for rapidly and broadly detecting the toxicity of sample cells.

It is another object of the present invention to provide a useful system including the above mentioned biosensor for rapidly and broadly detecting the toxicity of sample cells.

It is still another object of the present invention to provide a method of rapidly and broadly detecting the toxicity of sample cells.

In one aspect, the invention provides a biosensor for detecting the toxicity of a sample including a solid-state area image pickup element, a culture container positioned on an upper surface of a light-receiving portion of the element, at least a bottom surface of the culture container being formed of transparent material, a cell cultured in the culture container, and culture medium for growing the cell.

In a preferred embodiment, the bottom surface of the culture container is formed of any one member selected from the group consisting of a lens, a filter, a diaphragm, a pinhole, a slit, a deflecting plate, a light scattering plate, a color filter for picking out incident light having a specified wave length alone, or a combination thereof.

In another preferred embodiment, between the culture container and the element is positioned any one member selected from the group consisting of a lens, a filter, an iris, a pinhole, a slit, a deflecting plate, a light scattering plate, a color filter for picking out incident light having a specified wave length alone or a combination thereof.

In another aspect, the present invention provides a biosensor for detecting the toxicity of a sample including a solid-state area image pickup element, a culture container positioned on an upper surface of a light-receiving portion of the element, at least a bottom surface of the culture container being formed of transparent material, a cell cultured in the culture container, culture medium for growing said cell, and a light source for radiating light into the culture container.

In a preferred embodiment, the biosensor further includes a controller for controlling the strength of the light radiated from the light source in accordance with characteristics of the element.

In another preferred embodiment, the light source includes an electric-light bulb, a light emitting diode, and an electroluminescence element.

In still another preferred embodiment, the biosensor further includes an enclosure for interrupting external light to prevent it from entering the culture container.

In yet another preferred embodiment, the cell is positioned on the bottom surface of the culture container.

In still yet another preferred embodiment, the cell is selected from cells having high sensitivity to substances to be detected.

In another preferred embodiment, the cell includes a plurality of different kinds of cells.

In still another preferred embodiment, each kind of cells have their own area in which they are located on the bottom surface of the culture container.

In yet another preferred embodiment, the cell is a photogenic cell.

In still another aspect, the present invention provides a biosensor system for detecting the toxicity of a sample including at least one biosensor selected from the above mentioned biosensors, a driver for driving the element provided in the biosensor, and a display for receiving signals transmitted from the element and indicating data about the cell represented by the signals.

In still yet another aspect, the present invention provides a biosensor system for detecting the toxicity of a sample including at least one biosensor selected from the above mentioned biosensors, a controller which houses therein the biosensor to control external environment of the biosensor, a driver for driving the element provided in the biosensor, and a display for receiving signals transmitted from the element and indicating data about the cell represented by the signals.

In a further aspect, the present invention provides a biosensor system for detecting the toxicity of a sample including at least one biosensor selected from the above mentioned biosensors, a controller which houses therein the biosensor to control external environment of the biosensor and/or control the strength of the light radiated from the light source in accordance with characteristics of the element, a driver for driving the element provided in the biosensor, and a display for receiving signals transmitted from the element and indicating data about the cell represented by the signals.

In still a further aspect, the present invention provides a method of detecting the toxicity of a sample having the steps of positioning a culture container on an upper surface of a light-receiving portion of a solid-state area image pickup element, at least a bottom surface of the culture container being formed transparent material, providing a cell and culture medium in the culture container, providing a sample to be tested in the culture container so that the sample comes into contact with the cell, radiating external light over the cell, taking out data about the cell from the element, and indicating the data on a display.

In yet a further aspect, the present invention provides a method of detecting the toxicity of a sample including the steps of positioning a culture container on an upper surface of a light-receiving portion of a solid-state area image pickup element, at least a bottom surface of the culture container being formed transparent material, providing a cell and culture medium in the culture container, providing a sample to be tested in the culture container so that the sample comes into contact with the cell, radiating light over the cell with external light being interrupted so as to prevent it from entering the culture container, the strength of the light being controlled in accordance with characteristics of the element, taking out data about the cell from the element, and indicating the data on a display.

The advantages obtained by the aforementioned present invention will be described hereinbelow.

The biosensor and the system including the biosensor both in accordance with the present invention include a cell (or cells) and detect a change of cell morphology caused by the addition of a sample using the solid-state area image pickup element. Accordingly, the biosensor and the system including the biosensor can detect the cytotoxin of a sample particular to the cell. In addition, since the change of cell morphology is directly observed to detect the cytotoxin of a sample particular to the cell, steps such as adding reagent for measuring cell activity are not required. Thus, the test is quite simple. Furthermore, the toxicity of a sample including a plurality of different kinds of toxic substances can be detected without quantitative and qualitative analysis of each of the toxic substances.

The above and other objects and advantageous features of the present invention will be made apparent from the following description made with reference to the accompanying drawings.

DESCRIPTION OF THE PREFERRED EMBODIMENTS

Preferred embodiments in accordance with the invention will be explained hereinbelow with reference to drawings.

Figure 1:
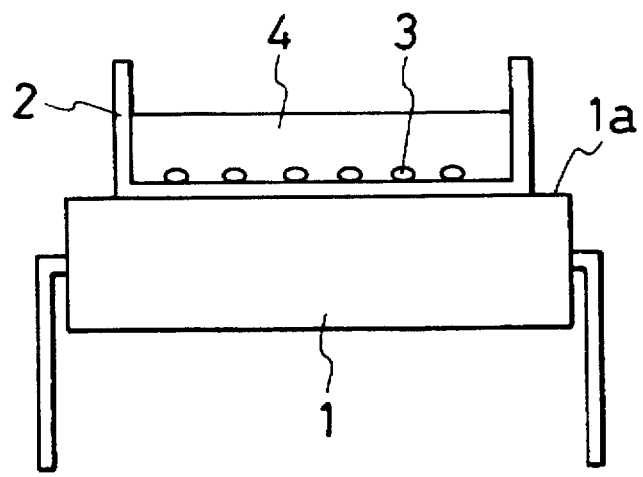
FIG. 1 is a schematic cross-sectional view illustrating a first embodiment of the biosensor in accordance with the invention.

FIG. 1 illustrates a first embodiment of a biosensor in accordance with the present invention. A solid-state area image pickup element 1 has an upper surface 1a having an object located thereon which is to be photographed. On the surface 1a is positioned a culture container 2 in which culture medium 4 is supplied. A plurality of cells 3 are provided in the culture medium 4 on a bottom surface of the culture container 2. Hereinbelow is explained how a test is carried out for determining whether a sample has toxicity or not. First the sample is put into the culture medium 4 and made in contact with the cells 3. A period of culture may be carried out, if necessary. Then, from the element 1 outputs 5 are taken out representing image data about extinction and damage of the cells 3 and change of the cell morphology. The determination of the toxicity of the sample is carried out by virtue of the outputs of the element 1.

Since the biosensor in the illustrated embodiment has the cells 3, data which the biosensor provides represent the toxicity particular to the cells 3. If the sample includes various toxic substances having various cytotoxin added at different rates, obtained data represent overall toxicity of the sample including the extent and amount of each toxic substances. Thus, since the biosensor in accordance with the embodiment judges the extent of damage of the cells 3 based on the above mentioned data, there is no need to measure cell activity, which makes the toxicity measurement quite simple.

Various kinds of cells may be used as the cell 3. A cell which prows attaching to a bottom surface of the culture container 2 is preferable than a cell which prows suspending in the culture medium 4 because in the former kind of cell, it is easier to observe cell morphology. The cells 3 are selected from those having high sensitivity to substances to be detected. For example, nerve cells are to be used for detecting neurotoxin or liver cells are to be used for detectin hepatotoxin. Alternatively, a plurality of different kinds of cells may be used. In such a case, each kind of cells may be positioned in different areas on a bottom surface of the culture container 2 so that forms of each kind of cells can be easily observed. The culture medium 4 is selected so as to be appropriate for the culture of cells to be used.

The biosensor needs to be radiated with light having strength suitable to characteristics of the element 1. External light is radiated over the culture container 2 and reaches the element 1 through the culture medium 4, the cells 3 and a bottom surface of the container 2. Thus, the forms of the cells 3 are detected by the element 1. For the purpose of passing light through the culture container 2 to the element 1, the container 2 may be entirely formed of transparent material. However, for the above mentioned purpose, at least a bottom surface of the culture container 2 is formed of light-pervious or transparent material, preferably transparent plastics such as transparent polystyrene or transparent glass.

Cells produced by gene manipulation to have photogenic substances may be applied to the biosensor in accordance with the invention. Even when the biosensor is to be used in darkness, the toxicity can be detected based on variation of the extent of light emission of the cells. In particular, the biosensor in accordance with the first embodiment illustrated in FIG. 1 has no light source, and hence photogenic substances are preferable when the biosensor is to be used in darkness.

Figure 2:
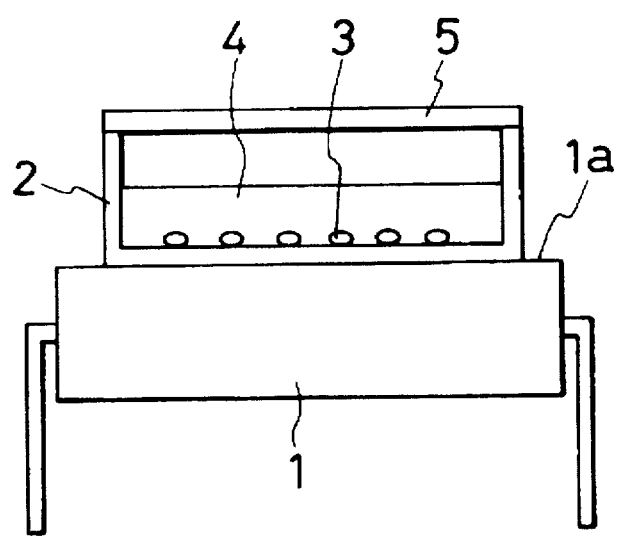
FIG. 2 is a schematic cross-sectional view illustrating a second embodiment of the biosensor in accordance with the invention.

FIG. 2 illustrates a second embodiment of a biosensor in accordance with the present invention. The biosensor illustrated in FIG. 2 can observe a non-photogenic sample by introducing external light into the culture container 2. The biosensor in FIG. 2 is the same as the biosensor in FIG. 1 except that the biosensor in FIG. 2 is provided with a filter 5 to cover the culture container 2 at an upper end thereof. The filter 5 weakens external light and thus introduces strength-controlled external light into the element 1. It is desirable that the light introduced to the element 1 has strength suitable to the characteristics of the element 1 and forwards in a common direction. Instead of the filter 5, there may be used a lens, an iris, a pinhole, a slit, a deflecting plate, a light scattering plate, a color filter for picking out incident light having a specified wave length alone or a combination thereof. The provision of the filter 5 or the above mentioned alternatives ensures that light suitable to the characteristics of the element 1 can be radiated to the element 1. This improves signals representing data about images of the cells. The filter 5 or its alternatives mentioned above may be placed between the bottom surface of the culture container 2 and the element 1. This arrangement brings the same result as the arrangement illustrated in FIG. 2. A lens system for image-formation may be placed between the culture container 2 and the element 1 in order to obtain clearer images of the cells 3.

Figure 3:
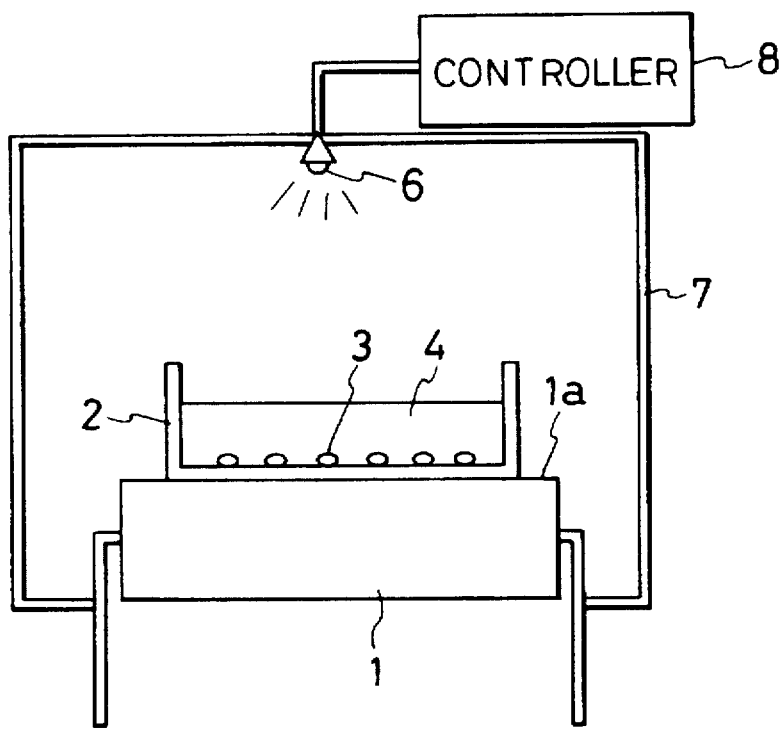
FIG. 3 is a schematic cross-sectional view illustrating a third embodiment of the biosensor in accordance with the invention.

FIG. 3 illustrates a third embodiment of the biosensor in accordance with the present invention. The biosensor illustrated in FIG. 3 is the same as the biosensor illustrated in FIG. 1 except that the biosensor illustrated in FIG. 3 is provided with a light source 6 to radiate light over the culture container 2 including therein the cells 3 and the culture medium 4, and an enclosure 7 for surrounding the culture container 2 and the upper surface 1a of the element 1 to prevent external light from entering therein. The light source 6 may be an electric-light bulb, a light emitting diode (LED) and an electroluminescence. The light source 6 is electrically connected with a controller 8 for adjusting the strength of light emitted from the light source 6 in accordance with the characteristics of the element 1. For instance, the controller 8 controls the voltage applied to the light source 6 to thereby control the strength of the radiated light. This arrangement ensures to obtain clearer images of the cells 3.

Hereinbelow is explained how the toxicity is detected using the biosensor as illustrated in FIG. 3. There was used an interline transfer type CCD as a solid-state area image pickup element, manufactured by NEC Corporation, the assignee, having a light-receiving surface of ½ inch size and having 683 by 492 pixels. On the light-receiving surface of the element was installed a culture container formed of transparent polystyrene and having a bottom surface of 20 mm by 15 mm, height of 10 mm and thickness of 0.5 mm. Into the culture container was provided MEM culture medium of 1 milliliter containing therein about 500,000 numbers of hepatocytes (HepG2). The culture container was left for 24 hours under the condition of temperature of 37 degrees centigrade, saturated humidity and carbon dioxide ($CO_2$) of 5% to thereby adhere the hepatocytes onto a bottom surface of the culture container. Then, the biosensor was connected to a driver and a high brightness type LED manufactured by Sharp Corporation under the trade name of "GL-5Ur3KT" was fixed 20 cm above the culture container so as to lighten the culture container. Then, carbon tetrachloride ($CCl_4$) was added into the container so that the content of $CCl_4$ was finally 5 millimol. The culture container was left for 3 hours under the condition of temperature of 37 degrees centigrade, saturated humidity and carbon dioxide ($CO_2$) of 5%. Then, the change of number and morphology of cells was recorded as data of images of the cells.

Figure 4:
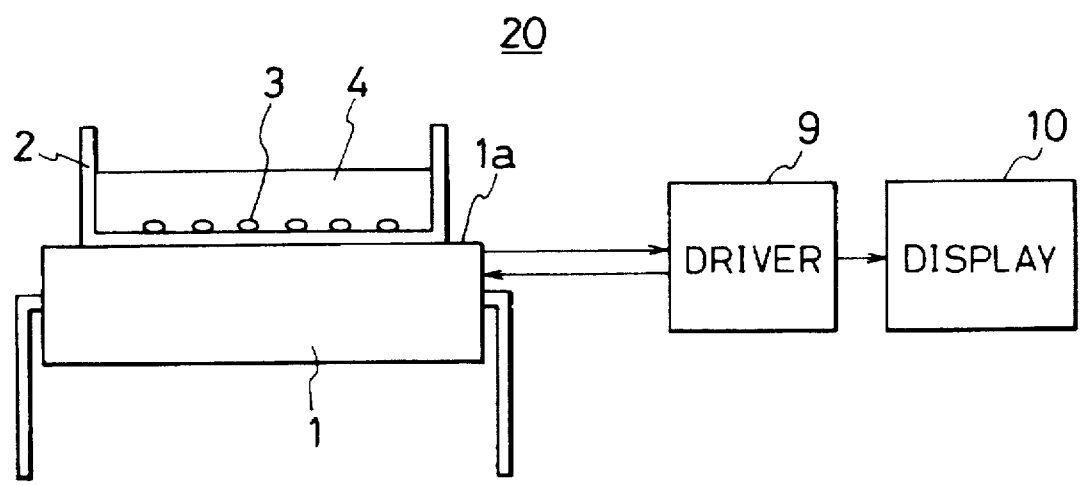
FIG. 4 is a schematic cross-sectional view illustrating an embodiment of the toxicity detecting system in accordance with the invention.

FIG. 4 illustrates an embodiment of the toxicity detecting system in accordance with the present invention. The system 20 includes the biosensor illustrated in FIG. 1. The system 20 may include the biosensor illustrated in FIG. 2. The element 1 provided in the biosensor is driven by a driver 9. The element 1 transmits the data of images of the cells 3 to a display 10 through the driver 9, and thus the images of the cells 3 are represented on the display 10. The display 10 may have functions of recording the images and digitizing the images as well as representing the images to thereby ensure more accurate observation of the cells 3. A plurality of the biosensors may be alternately connected to the single driver 9 and the single display 10, or a plurality sets of the biosensor and the driver 9 may be alternately connected to the single display 10. These systems make it possible to concurrently observe many samples.

Figure 5:
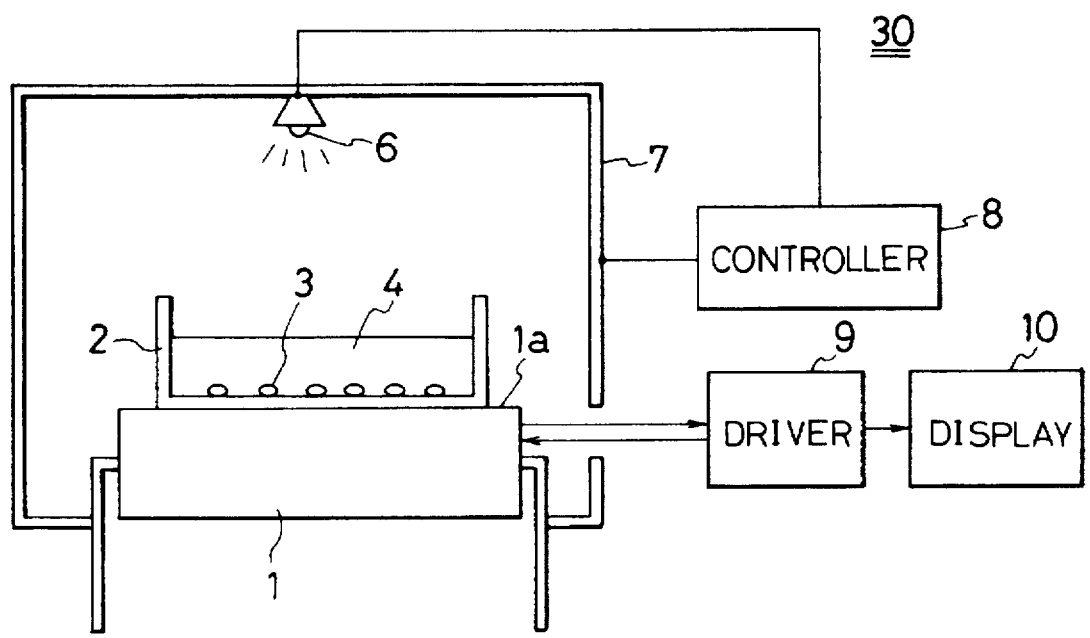
FIG. 5 is a schematic cross-sectional view illustrating another embodiment of the toxicity detecting system in accordance with the invention.

FIG. 5 illustrates another embodiment of the toxicity detecting system in accordance with the invention. The system 30 includes the biosensor illustrated in FIG. 3. Similarly to the embodiment illustrated in FIG. 4, the element 1 is driven by the driver 9 and transmits the data of images of the cells 3 to the display 10 through the driver 9. The images of the cells 3 are represented on the display 10. In this embodiment, the controller 8 controls the light source 6 to vary the strength of light radiated therefrom and also controls the conditions in the enclosure 7 such as the temperature, humidity and carbon dioxide content. Thus, the observation of the samples Can be carried out more accurately under the controlled condition. The system 30 is suitable particularly to successive observation of cells or bacteria. In particular, when a plurality of the biosensors is to be used to test a plurality of samples, the system 30 is quite suitable because the conditions of observation is all the same in each biosensor.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A biosensor for detecting the toxicity of a sample comprising:
    a solid-state area image pickup element;
    a culture container positioned on an upper surface of a light-receiving portion of said element, a bottom surface of said culture container being formed of one of transparent plastics and transparent glass;
    a cell cultured in said culture container; and
    culture medium for growing said cell.

2. A biosensor in accordance with claim 1, wherein between said culture container and said element is positioned any one selected from the group consisting of a lens, a filter, an iris, a pinhole, a slit, a deflecting plate, a light scattering plate, a color filter for picking out incident light having a specified wave length and a combination thereof.

3. A biosensor for detecting the toxicity of a sample comprising:
    a solid-state area image pickup element;
    a culture container positioned on an upper surface of a light-receiving portion of said element, a bottom surface of said culture container being formed of one of transparent plastics and transparent glass;
    a cell cultured in said culture container;
    culture medium for growing said cell; and
    a light source for radiating light toward said culture container.

4. A biosensor in accordance with claim 3 further comprising a controller for controlling the strength of the light radiated from said light source.

5. A biosensor in accordance with claim 3, wherein said light source is selected from the group consisting of an electric-light bulb, a light emitting diode, and an electroluminescence.

6. A biosensor in accordance with claim 3 further comprising an enclosure for interrupting external light so as not to enter said culture container, said light source being disposed in said enclosure.

7. A biosensor in accordance with claim 1, wherein said cell is positioned on the bottom surface of said culture container.

8. A biosensor in accordance with claim 1, wherein said cell is selected from cells having high sensitivity to substances to be detected.

9. A biosensor in accordance with claim 1, wherein a plurality of kinds of cells are cultured in said culture container.

10. A biosensor in accordance with claim 3, wherein a plurality of kinds of cells are cultured in said culture container.

11. A biosensor in accordance with claim 9, wherein each kind of cell has its own area in which it is located on said bottom surface of said culture container.

12. A biosensor in accordance with claim 10, wherein each kind of cell has its own area in which it is located on said bottom surface of said culture container.

13. A biosensor in accordance with claim 1, wherein said cell is a photogenic one.

14. A biosensor system for detecting the toxicity of a sample comprising:
    at least one biosensor in accordance with claim 1; and
    a driver for driving said element provided in said biosensor.

15. A biosensor system for detecting the toxicity of a sample comprising:
    at least one biosensor in accordance with claim 3; and
    a driver for driving said element provided in said biosensor.

16. A method of detecting the toxicity of a sample comprising the steps of:
    positioning a culture container on an upper surface of a light-receiving portion of a solid-state area image pickup element, a bottom surface of said culture container being formed of one of transparent plastics and transparent glass;
    providing a cell and culture medium in said culture container;
    providing a sample to be tested in said culture container so that the sample comes into contact with said cell;
    radiating external light over said cell;
    taking out data about said cell from said element; and
    indicating said data on a display.

17. A method of detecting the toxicity of a sample comprising the steps of:
    positioning a culture container on an upper surface of a light-receiving portion of a solid-state area image pickup element, a bottom surface of said culture container being formed of one of transparent plastics and transparent glass;
    providing a cell and culture medium in said culture container;
    providing a sample to be tested in said culture container so that the sample comes into contact with said cell;
    radiating light over said cell with external light being interrupted so as not to enter said culture container, the strength of said light being controlled by a controller;
    taking out data about said cell from said element; and
    indicating said data on a display.

* * * * *